(12) United States Patent
Kiji

(10) Patent No.: US 10,966,427 B2
(45) Date of Patent: Apr. 6, 2021

(54) 3-PYRIDYL OXYANILIDE COMPOUND AND USE THEREFOR

(71) Applicant: SUMITOMO CHEMICAL COMPANY, LIMITED, Tokyo (JP)

(72) Inventor: Toshiyuki Kiji, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/627,216

(22) PCT Filed: Aug. 17, 2018

(86) PCT No.: PCT/JP2018/030460
§ 371 (c)(1),
(2) Date: Dec. 27, 2019

(87) PCT Pub. No.: WO2019/035477
PCT Pub. Date: Feb. 21, 2019

(65) Prior Publication Data
US 2020/0120934 A1    Apr. 23, 2020

(30) Foreign Application Priority Data

Aug. 18, 2017  (JP) .............................. JP2017-157833
Feb. 28, 2018  (JP) .............................. JP2018-034373

(51) Int. Cl.
*C07D 401/14*   (2006.01)
*A01N 43/54*    (2006.01)

(52) U.S. Cl.
CPC ........... *A01N 43/54* (2013.01); *C07D 401/14* (2013.01)

(58) Field of Classification Search
CPC .................................................. C07D 401/14
See application file for complete search history.

(56) References Cited

U.S. PATENT DOCUMENTS 6,537,948 B1   3/2003   Tohyama et al.

FOREIGN PATENT DOCUMENTS

| EP | 1 122 244 A1 | 8/2001 |
|---|---|---|
| JP | 5-39272 A | 2/1993 |
| JP | 2002-155061 A | 5/2002 |
| JP | 2008-522965 A | 7/2008 |
| WO | WO 2006/061562 A1 | 6/2006 |
| WO | WO 2011/137088 A1 | 11/2011 |

OTHER PUBLICATIONS

International Preliminary Report on Patentability and the Written Opinion of the International Searching Authority for International Application No. PCT/JP2018/030460, dated Feb. 18, 2020.
International Search Report for International Application No. PCT/JP2018/030460 dated Nov. 13, 2018.

*Primary Examiner* — Paul V Ward
(74) *Attorney, Agent, or Firm* — Birch, Stewart, Kolasch & Birch, LLP

(57) ABSTRACT

The present invention provides a compound represented by formula (1), which has an excellent control efficacy against weeds, and is thus useful as an active ingredient for herbicidal composition.

3 Claims, No Drawings

3-PYRIDYL OXYANILIDE COMPOUND AND USE THEREFOR

TECHNICAL FIELD

This application claims priority to and the benefit of Japanese Patent Application Nos. 2017-157833 filed on Aug. 18, 2017 and 2018-034373 filed on Feb. 28, 2018, the entire contents of which are incorporated herein by reference.

The present invention relates to a 3-pyridyloxyanilide compound and its usage.

BACKGROUND ART

Some compounds showing some control effect against weeds are disclosed (see Patent Documents 1 and 2).

CITATION LIST

Patent Document

Patent Document 1: WO 2011/137088 Pamphlet
Patent Document 2: U.S. Pat. No. 6,537,948 B2

SUMMARY OF THE INVENTION

Problems to be Solved by Invention

An object of the present invention is to provide a compound having excellent control efficacy on weeds.

Means to Solve Problems

The present inventor has intensively studied that a compound represented by the following formula has some excellent efficacy on controlling weeds, which thus completed the present invention.

That is, the present invention provides the followings.
[1] A compound represented by formula (1):

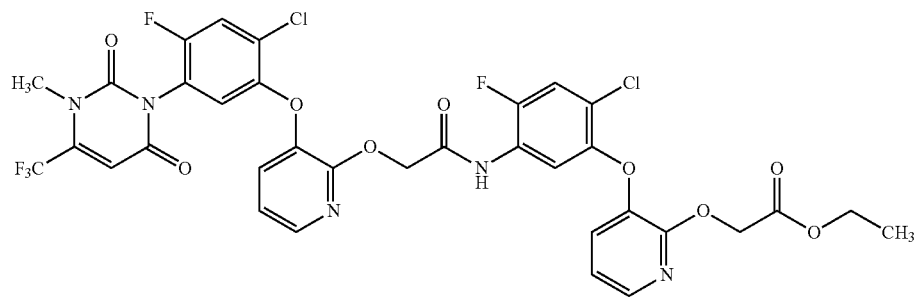

(1)

(hereinafter, referred to as "Present compound" or "Compound of the present invention").

[2] A herbicidal composition comprising the compound according to [1] and inert carrier (hereinafter, referred to as "Present herbicidal composition" or "Herbicidal composition of the present invention").

[3] A method for controlling weeds which comprises a step of applying the compound according to [1] to weeds or a place where weeds are growing or will grow (hereinafter, referred to as "Present control method against weeds" or "Method for controlling weeds of the present invention").

Effect of Invention

The present compound has an excellent control efficacy on weeds, and is effective as an active ingredient for herbicidal composition. Also the present compound has low phytotoxicity against useful plants, and shows high safety, and is effective as an active ingredient for herbicidal composition.

DESCRIPTION OF EMBODIMENTS

The present herbicidal composition comprises the present compound and inert carrier. The present herbicidal composition is usually prepared by mixing the present compound with an inert carrier such as solid carrier and liquid carrier, and optionally adding surfactants and other auxiliary agents for formulation, to formulate into wettable powders, water dispersible granules, flowables, granules, dry flowables, emulsifiable concentrates, or microcapsules. These formulations usually contain the present compound in a weight ratio of 0.1 to 99%.

Examples of the solid carrier to be used in the formulation include fine powders or granules of clays (for example, kaolin clay, diatomaceous earth, bentonite, Fubasami clay, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, or vinyl chloride-propylene copolymers).

Examples of the liquid carriers include water; alcohols (for example, methanol or ethanol); ketones (for example, acetone or methyl ethyl ketone); aromatic hydrocarbons (for example, toluene, xylene, ethyl benzene, or methylnaphthalene); aliphatic hydrocarbons (for example, hexane, cyclohexane, or kerosene); esters (for example, ethyl acetate or butyl acetate); nitriles (for example, acetonitrile or isobutyronitrile); ethers (for example, diisopropyl ether); amides (for example, N,N-dimethylformamide (DMF) or N,N-dimethylacetamide); sulfoxides (for example, dimethyl sulfoxide); propylene carbonate, and vegetable oils (for example, soybean oil or cottonseed oil).

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer, and specific examples include casein, gelatin, polysaccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

The method for controlling weeds of the present invention comprises a step of applying an effective amount of the present compound to weeds or a place where weeds are growing or will grow. In the method for controlling weeds of the present invention, usually, the present compound is used in the form of the herbicidal composition of the present invention. Examples of the method for controlling weeds of the present invention include a method of applying the present herbicidal composition to stems and leaves of weeds, a method of applying the present herbicidal composition to a surface of soil where weeds are growing or will grow, a method of incorporating the present herbicidal composition into soil where weeds are growing, and a method of applying the present herbicidal composition to a surface water of paddy field whose area where weeds are growing or will grow is flooded. In the method for controlling weeds of the present invention, the present compound is used usually 5 to 5,000 g, preferably 10 to 1,000 g per one (1) hectare of an area of a place where weeds are controlled.

The present compound may be used in an agricultural land and the like where useful plants as crops are grow to control weeds in the agricultural land.

Examples of the useful plants include the followings.

corn, rice, wheat, barley, rye, oat, *Sorghum*, cotton, soybean, peanut, sugar beet, rapeseed, sunflower, sugar cane, tobacco, and hops, etc.;

Solanaceous vegetables (such as eggplant, tomato, bell pepper, pepper, and potato, etc.);

Cucurbitaceous vegetables (such as cucumber, pumpkin, zucchini, watermelon, melon, and squash, etc.);

Cruciferous vegetables (such as Japanese radish, turnip, horseradish, kohlrabi, Chinese cabbage, cabbage, leaf mustard, broccoli, and cauliflower, etc.);

Asteraceous vegetables (such as burdock, crown daisy, artichoke, and lettuce, etc.);

Liliaceous vegetables (such as green onion, onion, garlic, and asparagus, etc.);

Umbelliferous vegetables (such as parsley, celery, and parsnip, etc.); Chenopodiaceous vegetables (such as spinach, and Swiss chard, etc.);

Lamiaceous vegetables (such as *Perilla frutescens*, mint, and basil, etc.);

Leguminous vegetables (such as green pea, kidney bean, adzuki bean, broad bean, and chickpea, etc.);

strawberry, sweet potato, Dioscorea japonica, colocasia, Elephant roots, ginger, and okra, etc.;

Pomaceous fruits (such as apple, Japanese pear, common pear, Chinese quince, and quince);

Stone fleshy fruits (such as peach, plum, nectarine, Japanese plum, cherry, apricot, and prune, etc.);

Citrus plants (such as Satsuma mandarin, orange, lemon, lime, and grapefruit, etc.);

Nuts (such as chestnut, walnut, hazel nut, almond, pistachio, cashew nut, and macadamia nut, etc.);

Berry fruits (such as blueberry, cranberry, blackberry, and raspberry, etc.);

grape, persimmon, olive, loquat, banana, coffee, date, coconut palm, and oil palm, etc.

The useful plants described above include also genetically-engineered plants.

Examples of the subjects to be controlled by the present compound include one or more kinds of the followings.

Urticaceae weeds: for example, *Urtica urens;*

Polygonaceae weeds: for example, *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius,* or *Rumex acetosa,* etc.;

Portulacaceae weeds: for example, *Portulaca oleracea,* etc.;

Caryophyllaceae weeds: for example, *Stellaria media, Stellaria aquatica, Cerastium holosteoides, Cerastium glomeratum, Spergula arvensis,* or *Silene gallica,* etc.;

Molluginaceae weeds: for example, *Mollugo verticillata,* etc.;

Chenopodiaceae weeds: for example, *Chenopodium album, Chenopodium ambrosioides, Kochia scoparia, Salsola kali,* or *Atriplex* spp., etc.;

Amaranthaceae weeds: for example, *Amaranthus retroflexus, Amaranthus viridis, Amaranthus lividus, Amaranthus spinosus, Amaranthus hybridus, Amaranthus palmeri, Amaranthus patulus, Amaranthus tuberculatus, Amaranthus blitoides, Amaranthus deflexus, Amaranthus quitensis, Alternanthera philoxeroides, Alternanthera sessilis,* or *Alternanthera tenella,* etc.;

Papaveraceae weeds: for example, *Papaver rhoeas, Papaver dubium,* or *Argemone mexicana,* etc.;

Brassicaceae weeds: for example, *Raphanus raphanistrum, Raphanus sativus, Sinapis arvensis, Capsella bursa-pastoris, Brassica juncea, Brassica napus, Descurainia pinnata, Rorippa islandica, Rorippa sylvestris, Thlaspi arvense, Myagrum rugosum, Lepidium virginicum,* or *Coronopus didymus,* etc.;

Capparaceae weeds: for example, *Cleome affinis,* etc.;

Fabaceae weeds: for example, *Aeschynomene indica, Aeschynomene rudis, Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxillensis,* or *Vigna sinensis,* etc.;

Oxalidaceae weeds: for example, *Oxalis corniculata, Oxalis strica,* or *Oxalis oxyptera,* etc.;

Geraniaceae weeds: for example, *Geranium carolinense,* or *Erodium cicutarium,* etc.;

Euphorbiaceae weeds: for example, *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis,* or *Ricinus communis,* etc.;

Malvaceae weeds: for example, *Abutilon theophrasti, Sida rhombifolia, Sida cordifolia, Sida spinosa, Sida glaziovii, Sida santaremnensis, Hibiscus trionum, Anoda cristata,* or *Malvastrum coromandelianum,* etc.;

Onagraceae weeds: for example, *Ludwigia epilobioides, Ludwigia octovalvis, Ludwigia decurre, Oenothera biennis,* or *Oenothera laciniata,* etc.;

Sterculiaceae weeds: for example, *Waltheria indica,* etc.;

Violaceae weeds: for example, *Viola arvensis,* or *Viola tricolor,* etc.;

Cucurbitaceae weeds: for example, *Sicyos angulatus, Echinocystis lobata,* or *Momordica charantia,* etc.;

Lythraceae weeds: for example, *Ammannia multiflora, Ammannia auriculata, Ammannia coccinea, Lythrum salicaria,* or *Rotala indica,* etc.;

Elatinaceae weeds: for example, *latine triandra,* or *Elatine californica,* etc.;

Apiaceae weeds: for example, *Oenanthe javanica, Daucus carota,* or *Conium maculatum,* etc.;

Araliaceae weeds: for example, *Hydrocotyle sibthorpioides,* or *Hydrocotyle ranunculoides,* etc.;

Ceratophyllaceae weeds: for example, *Ceratophyllum demersum,* etc.;

Cabombaceae weeds: for example, *Cabomba caroliniana,* etc.;

Haloragaceae weeds: for example, *Myriophyllum aquaticum, Myriophyllum verticillatum, Myriophyllum spicatum,* or *Myriophyllum heterophyllum,* etc.;

Sapindaceae weeds: for example, *Cardiospermum halicacabum,* etc.;

Primulaceae weeds: for example, *Anagallis arvensis,* etc.;

Asclepiadaceae weeds: for example, *Asclepias syriaca,* or *Ampelamus albidus,* etc.;

Rubiaceae weeds: for example, *Galium aparine, Galium spurium* var. *echinospermon, Spermacoce latifolia, Richardia brasiliensis,* or *Borreria alata,* etc.;

Convolvulaceae weeds: for example, *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides,* or *Jacquemontia tamnifolia,* etc.;

Boraginaceae weeds: for example, *Myosotis arvensis,* etc.;

Lamiaceae weeds: for example, *Lamium purpureum, Lamium amplexicaule, Leonotis nepetaefolia, Hyptis suaveolens, Hyptis lophanta, Leonurus sibiricus,* or *Stachys arvensis,* etc.;

Solanaceae weeds: for example, *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata,* or *Nicandra physaloides,* etc.;

Scrophulariaceae weeds: for example, *Veronica hederaefolia, Veronica persica, Veronica arvensis, Lindernia procumbens, Lindernia dubia, Lindernia angustifolia, Bacopa rotundifolia, Dopatrium junceum,* or *Gratiola japonica,* etc.;

Plantaginaceae weeds: for example, *Plantago asiatica, Plantago lanceolata, Plantago major,* or *Callitriche palustris,* etc.;

Asteraceae weeds: for example, *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza smatrensis, Conyza canadensis, Ambrosia artemisiaefolia, Ambrosia trifida, Bidens tripartita, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis, Eclipta prostrata, Eclipta alba,* or *Centipeda minima,* etc.;

Alismataceae weeds: for example, *Sagittaria pygmaea, Sagittaria trifolia, Sagittaria sagittifolia, Sagittaria montevidensis, Sagittaria aginashi, Alisma canaliculatum,* or *Alisma plantago-aquatica,* etc.;

Limnocharitaceae weeds for example, *Limnocharis flava,* etc.;

Hydrocharitaceae weeds: for example, *Limnobium spongia, Hydrilla verticillata,* or *Najas guadalupensis,* etc.;

Araceae weeds: for example, *Pistia stratiotes,* etc.;

Lemnaceae weeds: for example, *Lemna aoukikusa, Spirodela polyrhiza,* or *Wolffia* spp., etc.;

Potamogetonaceae weeds: for example, *Potamogeton distinctus, Potamogeton crispus, Potamogeton illinoensis,* or *Stuckenia pectinata,* etc.;

Liliaceae weeds: for example, *Allium canadense, Allium vineale,* or *Allium macrostemon,* etc.;

Pontederiaceae weeds: for example, *Eichhornia crassipes, Heteranthera limosa, Monochoria korsakowii,* or *Monochoria vaginalis,* etc.;

Commelinaceae weeds: for example, *Commelina communis, Commelina bengharensis, Commelina erecta,* or *Murdannia keisak,* etc.;

Poaceae weeds: for example, *Echinochloa crus-galli, Echinochloa oryzicola, Echinochloa crus-galli* var *formosensis, Echinochloa oryzoides, Echinochloa colona, Echinochloa crus-pavonis, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Poa trivialis, Poa pratensis, Alospecurus aequalis, Alopecurus myosuroides, Avena fatua, Sorghum halepense, Sorghum vulgare, Agropyron repens, Lolium multiflorum, Lolium perenne, Lolium rigidum, Bromus catharticus, Bromus sterilis, Bromus japonicus, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Chlorisvirgata, Eragrostis pilosa, Rhynchelitrum repens, Dactyloctenium aegyptium, Ischaemum rugosum, Isachne globosa, Oryza sativa, Paspalum notatum, Paspalum maritimum, Paspalum distichum, Pennisetum clandestinum, Pennisetum setosum, Rottboellia cochinchinensis, Leptochloa chinensis, Leptochloa fascicularis, Leptochloa filiformis, Leptochloa panicoides, Leersia japonica, Leersia sayanuka, Leersia oryzoides, Glyceria leptorrhiza, Glyceria acutiflora, Glyceria maxima, Agrostis gigantea, Agrostis stolonifera, Cynodon dactylon, Dactylis glomerata, Eremochloa ophiuroides, Festuca arundinacea, Festuca rubra, Imperata cylindrica, Miscanthus sinensis, Panicum virgatum,* or *Zoysia japonica,* etc.;

Cyperaceae weeds: for example, *Cyperus microiria, Cyperus iria, Cyperus compressus, Cyperus difformis, Cyperus flaccidus, Cyperus globosus, Cyperus nipponics, Cype-* rus odoratus, Cyperus serotinas, Cyperus rotundas, Cyperus esculentus, Kyllinga gracillima, Kyllinga brevifolia, Fimbristylis miliacea, Fimbristylis dichotoma, Eleocharis acicularis, Eleocharis kuroguwai, Schoenoplectiella hotarui, Schoenoplectiella juncoides, Schoenoplectiella wallichii, Schoenoplectiella mucronatus, Schoenoplectiella triangulatus, Schoenoplectiella nipponicus, Schoenoplectiella triqueter, Bolboschoenus koshevnikovii, or Bolboschoenus fluviatilis, etc.;

Equisetaceae weeds: for example, Equisetum arvense, or Equisetum palustre, etc.;

Salviniaceae weeds: for example, Salvinia natans, etc.;

Azollaceae weeds: for example, Azolla japonica, or Azolla imbricata, etc.;

Marsileaceae weeds: for example, Marsilea quadrifolia, etc.;

Others: filamentous algae (for example, Pithophora, Cladophora), mosess, liverwort, hornwort, cyanobacteria, bracken, and sucker of permanent crops (for example, pome fruits, stone fruits, berry fruits, nut fruit, citrus fruit, hop, or grapes etc.).

EXAMPLES

Hereinafter, the present invention is explained in more detail by using Preparation Examples, Formulation Examples, and Test Examples, however, the present invention is not limited thereto.

Preparation Example

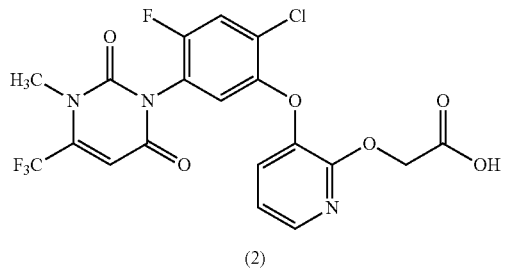

(2)

+

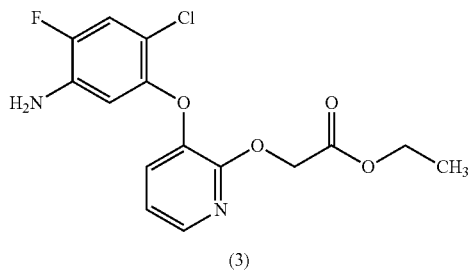

(3)

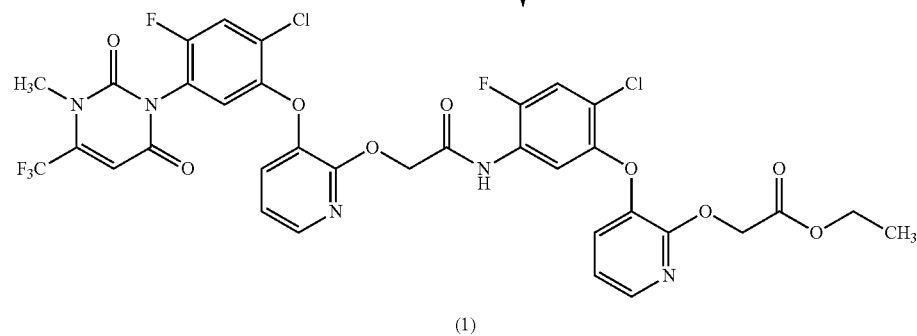

(1)

To a mixture of a compound represented by formula (2) 1.64 g, and a compound represented by formula (3) 1.20 g, and tetrahydrofuran 16.50 g was added N,N'-dicyclohexylcarbodiimide (hereinafter referred to as DCC) 0.89 g at room temperature (hereinafter referred to as RT), and the mixture was stirred for three hours. To the mixture was added DCC 0.21 g, and the resulting mixture was stirred at RT for two hours. To the mixture was added the compound represented by formula (3) 0.25 g, and the resulting mixture was stirred at RT for two hours. To the mixture was added DCC 0.21 g, and the resulting mixture was stirred at RT for three hours. The reaction mixture was filtered, and the filtrates were concentrated. The resulting residues were purified by silica gel chromatography (ethyl acetate:hexane=1:1) to obtain the present compound 2.08 g.

$^1$H-NMR value of the present compound is indicated below.

$^1$H-NMR (CDCl$_3$) δ: 1.23 (3H, t), 3.49 (3H, d), 4.21 (2H, q), 4.95 (2H, s), 4.96 (2H, s), 6.30 (1H, s), 6.80 (1H, d), 6.85 (1H, dd), 7.00 (1H, dd), 7.06 (1H, dd), 7.20 (1H, d), 7.31 (1H, dd), 7.42 (1H, d), 7.85 (1H, dd), 7.97 (1H, dd), 8.07 (1H, d), 8.38 (1H, br).

The compound represented by formula (2) and the compound represented by formula (3) may be prepared, for example, by the method described in U.S. Pat. No. 6,537,948 B2.

Next, Formulation Examples of the present compound are described. Herein, the term "part(s)" means "part(s) by weight".

Formulation Example 1

Fifty (50) parts of the present compound, 5 parts of sodium lignin sulfonate, 5 parts of polyoxyethylenealkylether, 5 parts of wet silica, and 35 parts of clay are mixed thoroughly to obtain a formulation.

Formulation Example 2

To 1.5 parts of the present compound, 2 parts of sodium lignin sulfonate, 40 parts of talc, and 56.5 parts of bentonite are added, followed by mixing. Next, an appropriate amount of water is added to the mixture, and the resulting mixture is further stirred, and is granulated with a granulator, and is forced-air dried to obtain a formulation.

Formulation Example 3

Thirty-five (35) parts of a mixture of Polyoxyethylene alkyl ether sulfate ammonium salt and wet silica (weight ratio of 1:1), 10 parts of the present compound, and 55 parts of water are mixed thoroughly to obtain a formulation.

Further, a herbicide efficacy of the present compound is shown by Test Examples.

In the following test examples, the assessment of the herbicide efficacy is assigned to a score of 0 to 10 as shown in Table 1, wherein "0" is defined if the condition of germination or growth of the tested weeds in the treated group indicates little or no difference compared to that of the untreated group at the timing of the investigation, and "10" is defined if the treated weeds were withered completely or their germination or growth was completely inhibited.

Here "untreated group" represents a group where a similar treatment procedure to that of the treated group except not using the test compound is done.

TABLE 1

| score | Herbicide efficacy |
|---|---|
| 10 | 100% of herbicide efficacy |
| 9 | 90% to 99% of herbicide efficacy |
| 8 | 80% to 89% of herbicide efficacy |
| 7 | 70% to 79% of herbicide efficacy |
| 6 | 60% to 69% of herbicide efficacy |
| 5 | 50% to 59% of herbicide efficacy |
| 4 | 40% to 49% of herbicide efficacy |
| 3 | 30% to 39% of herbicide efficacy |
| 2 | 20% to 29% of herbicide efficacy |
| 1 | 10% to 19% of herbicide efficacy |
| 0 | 0% to 9% of herbicide efficacy |

Test Example 1

One point one nine (1.19) mg of the present compound was dissolved 1 mL of a DMF solution containing 2% polyoxyethylene sorbitan monolaurate, and then 18 mL of water was added thereto. The mixture was sprayed uniformly to *Echinochloa crus-galli* in the second to third leaf stages so that the applied dose was made 63 g/ha. Thereafter, the plants were cultivated in a greenhouse for days, and the herbicide efficacy was assessed. As a result of the test, the present compound showed a score of 9 as herbicide efficacy.

Test Example 2

One point one nine (1.19) mg of the present compound was dissolved 1 mL of a DMF solution containing 2% polyoxyethylene sorbitan monolaurate, and then 18 mL of water was added thereto. The mixture was sprayed uniformly to *Digitaria ciliaris* in the second to third leaf stages so that the applied dose was made 63 g/ha. Thereafter, the plants were cultivated in a greenhouse for 7 days, and the herbicide efficacy was assessed. As a result of the test, the present compound showed a score of 9 as herbicide efficacy.

Test Example 3

*Leptochloa chinensis* seeds were seeded into a pot having a diameter of 9 cm and a death of 10 cm that was filled with steam-sterilized soil, and the plants were cultivated in a greenhouse until an emergence of the first leaf stage.

Next, 4.75 mg of the present compound was dissolved into a 1 mL of DMF solution containing 2% polyoxyethylene sorbitan monolaurate, and then 18 mL of water was added thereto. The mixture was sprayed uniformly to the pot so that the applied dose was made 250 g/ha. After the pot was flooded to a depth of 3 cm on next day, the plants were cultivated in a greenhouse for 20 days, and the herbicide efficacy was assessed. As a result of the test, the present compound showed a score of 10 as herbicide efficacy.

Furthermore, the safety of the present compound against useful plants as crop is shown by Test Examples.

In the following test examples, the assessment of the phytotoxicity is assigned to a score of 0 to 10 as shown in Table 2, wherein "0" is defined if the condition of germination or growth of the tested weeds in the treated group indicates little or no difference compared to that of the untreated group if the treated weeds were withered completely or their germination or growth was completely inhibited.

Here "untreated group" represents a group where a similar treatment procedure to that of the treated group except not using the test compound is done.

TABLE 2

| score | Phytotoxicity |
|---|---|
| 10 | 100% of phytotoxicity |
| 9 | 90% to 99% of phytotoxicity |
| 8 | 80% to 89% of phytotoxicity |
| 7 | 70% to 79% of phytotoxicity |
| 6 | 60% to 69% of phytotoxicity |
| 5 | 50% to 59% of phytotoxicity |
| 4 | 40% to 49% of phytotoxicity |
| 3 | 30% to 39% of phytotoxicity |
| 2 | 20% to 29% of phytotoxicity |
| 1 | 10% to 19% of phytotoxicity |
| 0 | 0% to 9% of phytotoxicity |

Test Example 4

One point one nine (1.19) mg of the present compound was dissolved 1 mL of a DMF solution containing 2% polyoxyethylene sorbitan monolaurate, and then 18 mL of water was added thereto. The mixture was sprayed uniformly to soybean in the second to third leaf stages so that the applied dose was made 63 g/ha. Thereafter, the plants were cultivated in a greenhouse for 7 days, and the phytotoxicity against useful plants was assessed. After a result of the test, the present compound showed a score of 2 as phytotoxicity.

Test Example 5

One point one nine (1.19) mg of the present compound was dissolved 1 mL of a DMF solution containing 2% polyoxyethylene sorbitan monolaurate, and then 18 mL of water was added thereto. The mixture was sprayed uniformly to *Digitaria ciliaris* in the second to third leaf stages so that the applied dose was made 63 g/ha. Thereafter, the plants were cultivated in a greenhouse for 16 days, and the herbicide efficacy was assessed.

Also, 1.19 mg of the present compound was dissolved 1 mL of a DMF solution containing 2% polyoxyethylene sorbitan monolaurate, and then 18 mL of water was added thereto. The mixture was sprayed uniformly to soybean in the second to third leaf stages so that the applied dose was made 63 g/ha. Thereafter, the plants were cultivated in a greenhouse for 16 days, and the phytotoxicity against useful plants was assessed.

The test results are shown in Table 3.

TABLE 3

| Test Compound | Applied dose [g/ha] | Herbicide efficacy against *digitaria ciliaris* | Phytotoxicity against Soybean |
|---|---|---|---|
| Present compound | 63 | 10 | 1 |

As shown in the above test Examples, the present compound showed excellent control efficacy against weeds. Further, the phytotoxicity of the present compound against soybean was low, which showed high safety against useful plants.

Comparative Example 1

The test was conducted similarly to the method described in Test Example 5 except for using a compound represented by the following formula (A):

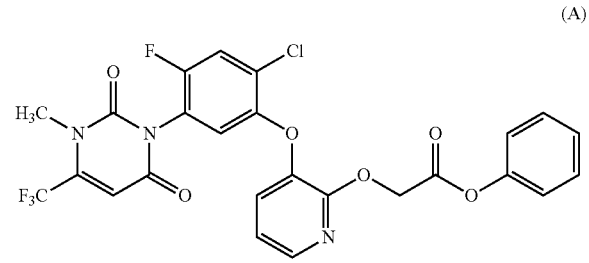 [SMILES: Cn1c(C(F)(F)F)cc(=O)n(-c2cc(Oc3cccnc3OCC(=O)Oc3ccccc3)c(Cl)cc2F)c1=O]

(hereinafter referred to as Compound (A)) which is described in U.S. Pat. No. 6,537,948 B2 instead of the present compound. The test results are shown in Table 4.

TABLE 4

| Test Compound | Applied dose [g/ha] | Herbicide efficacy against *digitaria ciliaris* | Phytotoxicity against Soybean |
|---|---|---|---|
| Compound (A) | 63 | 10 | 10 |

As shown in Table 4, Compound (A) showed excellent control efficacy against weeds. Meanwhile, Compound (A) showed high phytotoxicity against soybean as useful plants.

INDUSTRIAL APPLICABILITY

The present compound showed an excellent efficacy against weeds, and also showed low phytotoxicity against useful plants, which results in high safety, and thus the present compound is useful as an active ingredient for herbicidal composition.

The invention claimed is:
1. A compound represented by formula (1):

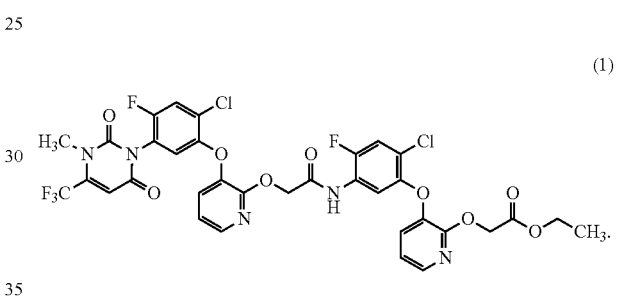

2. A herbicidal composition comprising the compound according to claim 1 and inert carrier.

3. A method for controlling weeds which comprises a step of applying the compound according to claim 1 to weeds or a place where weeds are growing or will grow.

* * * * *